(12) United States Patent
Carroll

(10) Patent No.: US 6,910,891 B2
(45) Date of Patent: Jun. 28, 2005

(54) DENTAL ABUTMENT HAVING RELIEF GROOVES

(76) Inventor: Ernest A. Carroll, 12913 Alton Sq., #114, Herndon, VA (US) 20170

( * ) Notice: Subject to any disclaimer, the term of this patent is extended or adjusted under 35 U.S.C. 154(b) by 288 days.

(21) Appl. No.: 10/244,009

(22) Filed: Sep. 16, 2002

(65) Prior Publication Data

US 2004/0053194 A1 Mar. 18, 2004

(51) Int. Cl.⁷ .................................................. A61C 8/00
(52) U.S. Cl. ..................................................... 433/173
(58) Field of Search ............................... 433/172, 173, 433/174, 175, 176

(56) References Cited

U.S. PATENT DOCUMENTS

| | | | |
|---|---|---|---|
| 4,988,298 A | | 1/1991 | Lazzara et al. |
| 5,658,147 A | * | 8/1997 | Phimmasone ............... 433/213 |
| 5,820,374 A | | 10/1998 | Simmons et al. |
| 5,897,320 A | | 4/1999 | Gittleman |
| 6,244,867 B1 | * | 6/2001 | Aravena et al. ............. 433/172 |
| 2002/0090592 A1 | * | 7/2002 | Riley et al. .................. 433/173 |

* cited by examiner

*Primary Examiner*—Cary E. O'Connor
(74) *Attorney, Agent, or Firm*—David L. Banner

(57) ABSTRACT

An abutment for mounting a restoration or crown to a dental implant, exhibiting ability to retain the restoration thereon and to prevent rotation of the restoration about the abutment. The abutment has a relatively wide base and a relatively slender tapered projection. A stepped hole passes through the abutment for receiving a screw which secures the abutment to the implant. The bottom of the stepped hole is hexagonal, for cooperatively receiving a hexagonal post of the dental implant. The base of the abutment has an inclined surface. The projection of the abutment has negative taper such that it is wider away from the base than where it joins the base. The projection has a groove formed therein, which groove extends along the abutment in a path which for at least part of the circumference of the abutment is neither purely horizontal nor purely vertical.

17 Claims, 4 Drawing Sheets

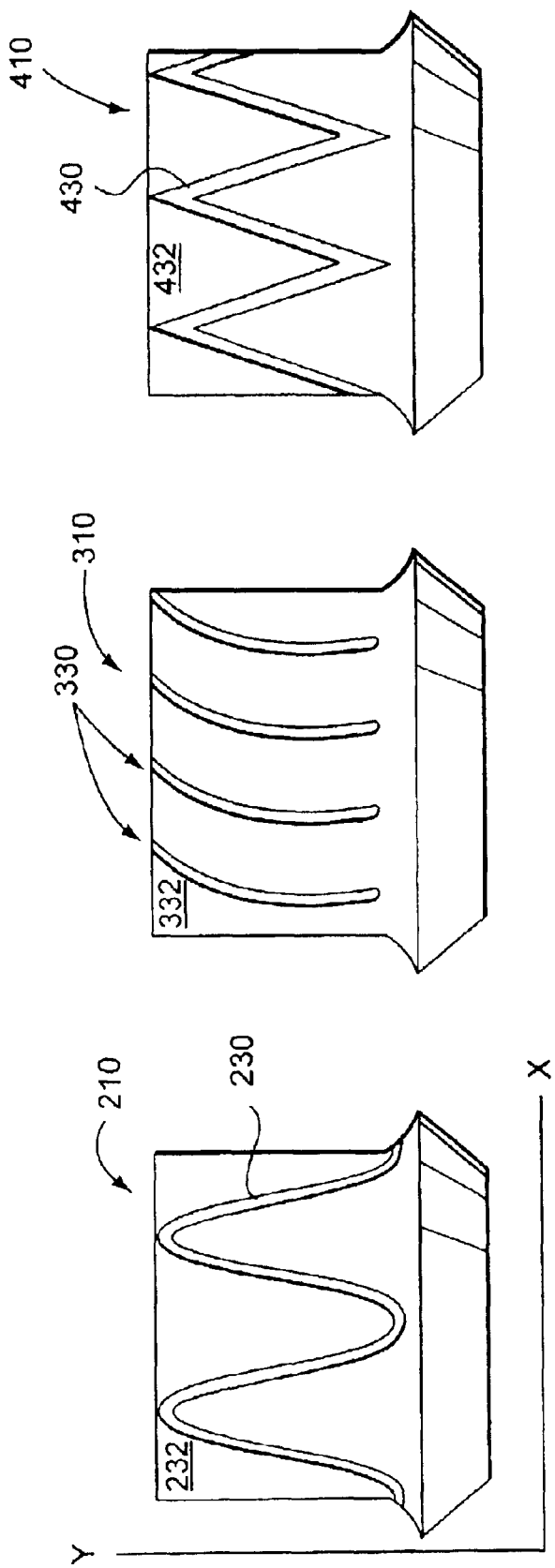

DENTAL ABUTMENT HAVING RELIEF GROOVES

REFERENCE TO RELATED APPLICATION

This application related to Ser. No. 09/838,221, filed Apr. 20, 2001.

BACKGROUND OF THE INVENTION

1. Field of the Invention

The present invention relates to abutments for dental prostheses implanted in the jawbone of a dental patient. More particularly, the invention provides an abutment post having grooves formed therein for carrying away fluids which would otherwise interfere with successful bonding of a restoration on the abutment post.

2. Description of the Prior Art

Replacement of lost teeth by prostheses individually anchored in the jaw has become a popular procedure. A complete prosthesis assembly includes an implant or anchor which is implanted in the jaw and becomes osseointegrated with bone tissue, an abutment which is received and supported within the implant, and a crown or restoration which simulates a natural tooth. The crown or restoration is typically cast from a suitable metallic alloy over the abutment, and is supported on the abutment. The crown or restoration typically has a porcelain or other ceramic coating for esthetic purposes. In a successful implant, only the restoration is visible, except for a plug which is visible from the top of the prosthesis. The plug closes a hole formed in the restoration for enabling a screw employed to secure the restoration to the implant. The screw passes through a hole formed in the restoration, and engages threads formed in the implant.

A successful implant and associated implant, if properly fabricated, will usually last for the life of the patient if properly fabricated. However, certain problems can arise from poorly fabricated restorations. One example is metal bubbles formed at abutting surfaces of the abutment and the restoration. Such bubbles can form when air and other gasses are not vented during casting of the restoration. Bubbles reduce engagement area of the restoration relative to the abutment, cause the abutment not to fit flush to the implant, destabilize the screw joint, and promote loosening of the screw. Another possible fault is thinness of the lowermost wall of the abutment where it covers and encircles the post of the abutment. This wall can spread, thereby losing grip on the abutment. Alternatively, an open area can be created between the restoration and the post of the abutment should the wall distort, thereby promoting growth of undesirable microorganisms in the mouth.

Still another problem which can arise is loss of proper orientation of the restoration with respect to the abutment. One example is withdrawal of the restoration from the abutment, illustratively where the former pulls free from the latter. In this case, the restoration could be swallowed or otherwise lost. Still another example is rotation of the restoration about the post of the abutment. This will result in angular misalignment of the prosthesis within the mouth, which could cause inability of the jaws to fully close, an objectionable esthetic situation, and a feeling of discomfort to the patient.

U.S. Pat. No. 4,988,298, issued to Richard J. Lazzara et al. on Jan. 29, 1991, illustrates an abutment having horizontal, circumferential grooves formed therein. In one embodiment, the present invention differs from the device of Lazzara et al. in having generally semi-elliptical grooves rather than the horizontal, circumferential grooves of Lazzara et al., and also in that the abutment has negative taper. Alternatively stated, the post of the abutment is tapered such that it is wider at the top or free end than it is at the bottom or base where it engages the implant. The groove of the present invention, when projected onto a sectional plane of the abutment, extends in both horizontal and vertical orthogonal axes as it encircles the abutment.

U.S. Pat. No. 5,820,374, issued to William F. Simmons et al. on Oct. 13, 1998, illustrates a dental implant having a textured exterior surface to improve osseointegration. The implant is not an abutment having either negative taper or grooves which extend in two orthogonal axes.

U.S. Pat. No. 5,897,320, issued to Neal B. Gittleman on Apr. 27, 1999, illustrates an abutment having relief channels formed therein to conduct excess dental cement away when cementing a prosthesis to an abutment. The channels include a vertical channel and a horizontal channel. Gittleman modifies the post of the abutment to receive the vertical channel and to accept a plug. By contrast, the generally frustoconical surface of the abutment post is not modified in the present invention other than by the groove itself, whereas Gittleman provides machined flat surfaces. This is difficult to fabricate, since a typical abutment is less than one quarter inch (six mm) in diameter.

Also, the plug of Gittleman must be very precisely formed to cooperate with its associated abutment. In the present invention, no such precision is necessary, since the groove may be formed on the exterior surface of the abutment post. The groove is preferably semi-elliptical in the present invention, and does not have a purely vertical channel and a purely horizontal channel, as taught by Gittleman. Also, the post of the present invention has negative taper in that it is wider at the top of the abutment than it is at the bottom of the abutment where the abutment contacts the implant. This feature is not shown in Gittleman.

None of the above inventions and patents, taken either singly or in combination, is seen to describe the instant invention as claimed.

SUMMARY OF THE INVENTION

The present invention sets forth an abutment for a dental prosthesis which has grooves formed thereon for assisting fabrication and retention of the restoration. The grooves extend along two orthogonal directions simultaneously for at least part of the circumference of the abutment, and are located and configured to conduct gasses away when casting the restoration to the abutment, and to immobilize the cast restoration relative to the abutment to maintain angular orientation. The novel groove is readily inscribed on the outer surface of the abutment by a computer numerical controlled (CNC) machine, and assists in overcoming the problem of trapped gas bubbles in the final restoration casting. Also, once the molten metal of the casting has hardened over the abutment and has entered the groove, the abutment and restoration are locked together so as to oppose axial movement and also rotation of one relative to the other.

The post of the abutment has negative taper. That is, it is wider at the top than it is at the base where the abutment has a hexagonal or other keyed portion for joining to the anchor of the implanted prosthesis. Negative taper assures that the restoration cannot be withdrawn from the abutment by pulling off. Another advantage of negative taper is that this configuration causes the lower skirt or wall of the cast portion of the restoration to have greater thickness than in restorations of the prior art and hence strength than would be the case if there were no taper.

Accordingly, it is one object of the invention to provide a dental abutment which promotes retention of a restoration thereto.

It is another object of the invention to promote evacuation of gasses from a mold when casting a restoration to an abutment.

It is a further object of the invention to assure that a restoration cast to an abutment be precluded from rotation therewith.

Still another object of the invention is to strengthen the lower wall of a restoration cast to an abutment.

An additional object of the invention is to prevent withdrawal of a restoration from its associated abutment.

Yet another object of the invention is to enable fabrication of a suitable groove for accomplishing the foregoing in an abutment by means of a CNC engraving machine.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein:

FIG. 7 is a side elevational view of another embodiment of the invention, showing an exaggerated sinusoidal groove.

FIG. 8 is a side elevational view of yet another embodiment of the invention, showing a discontinuous groove.

FIG. 9 is a side elevational view of still another embodiment of the invention, showing a further variation of a groove.

DETAILED DESCRIPTION OF THE PREFERRED EMBODIMENTS

Figure 1:
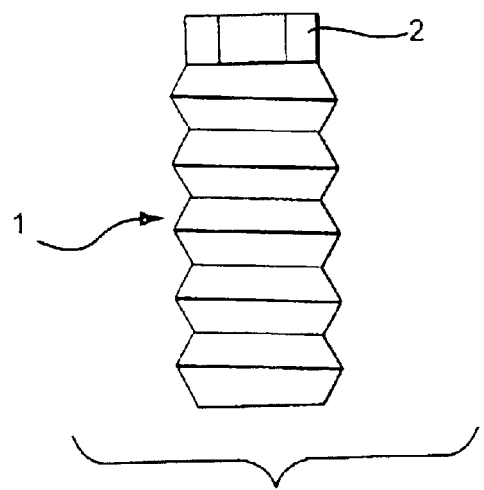
FIG. 1 is an environmental, side elevational view of one embodiment of the invention, shown partially in cross section.

Turning now to FIG. 1 of the drawings, 1 indicates a dental implant which is osseointegrated into the jaw (not shown) of a patient. Implant 1 has a hexagonal shaft 2 projecting upwardly therefrom. Novel abutment 10 has a restoration 3 cast thereto. A screw 4 passes through a stepped bore 12 formed in abutment 10, and will be tightened into a corresponding threaded hole (not shown) formed in implant 1. When head 5 of screw 4 contacts shoulder 14 of stepped bore 12, screw 4 will fasten abutment 10 to implant 1. Opening 6 of restoration 3 may then be suitably plugged to exclude bacteria and other contaminants from opening 6.

Figure 2:
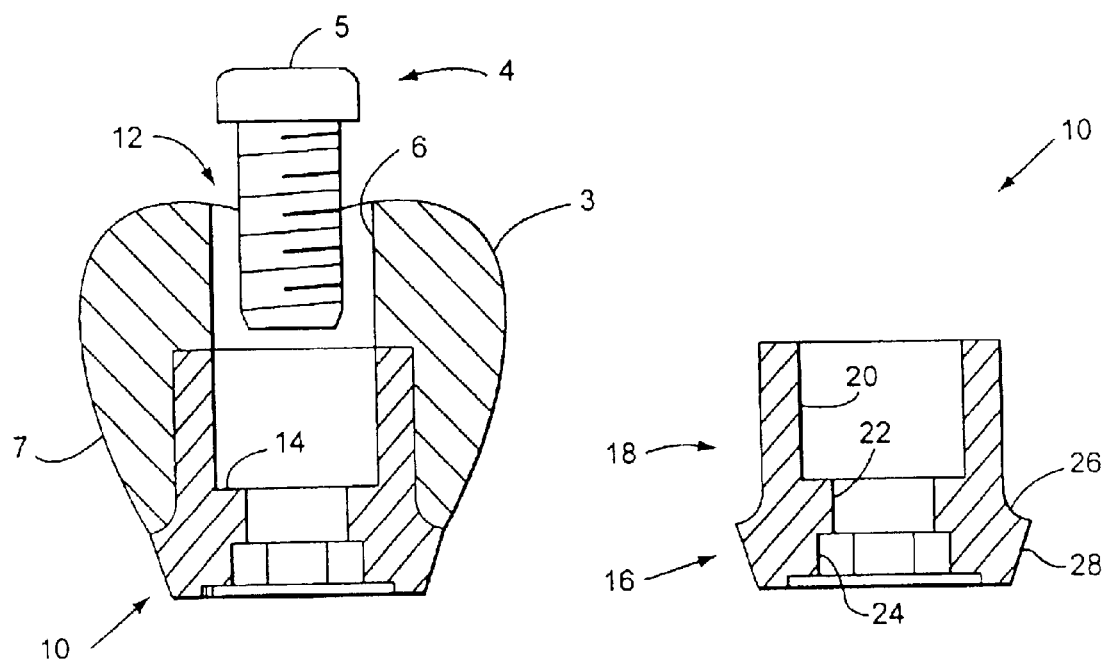
FIG. 2 is a cross sectional, side elevational view of the embodiment of FIG. 1.
Figure 5:
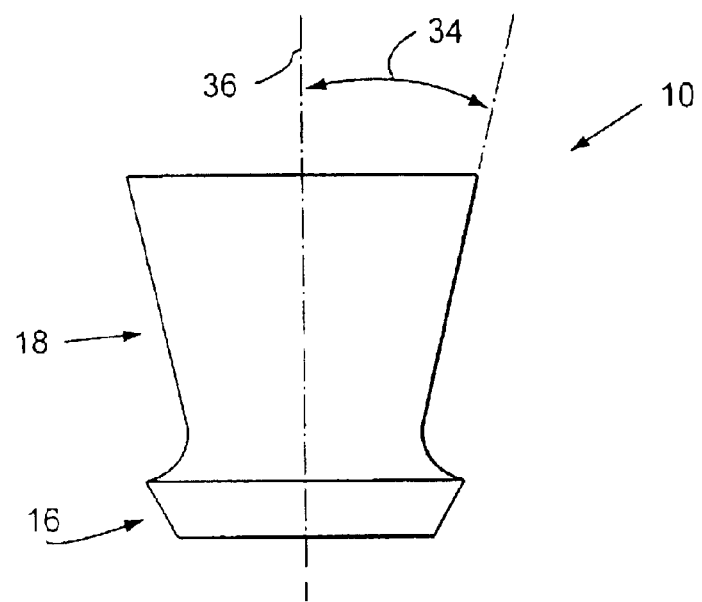
FIG. 5 is an exaggerated side elevational view of an abutment which is the subject of the present invention.

Structural features of abutment 10 will be described, with reference to FIG. 2. Abutment 10 has a base 16 of relatively great diameter and a tapered projection 18 of a relatively small diameter projecting upwardly from base 16. FIG. 5 shows the taper in an exaggerated view. It must be understood that as employed herein, directions such as upward and downward refer to the depictions as drawn. Implants and abutments can be inverted for installation in the upper jaw as well as being installed in the lower jaw. Therefore, vertical directions will be understood to be for semantic clarity only, and do not limit construction and usage of the invention.

Stepped bore 12 extends axially through both base 16 and tapered projection 18. Stepped bore 12 has a relatively large step 20 exposed from the direction of tapered projection 18 and a relatively small step 22 disposed below large step 20. A section 24 of stepped bore 12 disposed below small step 22 has keyed configuration exposed from below base 16, for cooperating with corresponding keyed configuration of implant 1. In most cases, the hexagonal shaft 2 is the keyed element of implant 1. However, the shaft could be square or otherwise configured. It is also possible that implant 1 will have a female member rather than shaft 2, which is male. This female member may be a square, hexagonal, or otherwise configured opening. The latter condition requires that the keyed element of the novel abutment have a square, hexagonal, or other corresponding male component (not shown) which cooperates with the female member of the implant.

Base 16 forms a concave curve 26 on the exterior of abutment 10 where base 16 joins tapered projection 18. Base 16 has a tapered exterior surface 28 such that base 16 is relatively wide proximate tapered projection 18 and is relatively narrow away from tapered projection 18.

Figure 3:
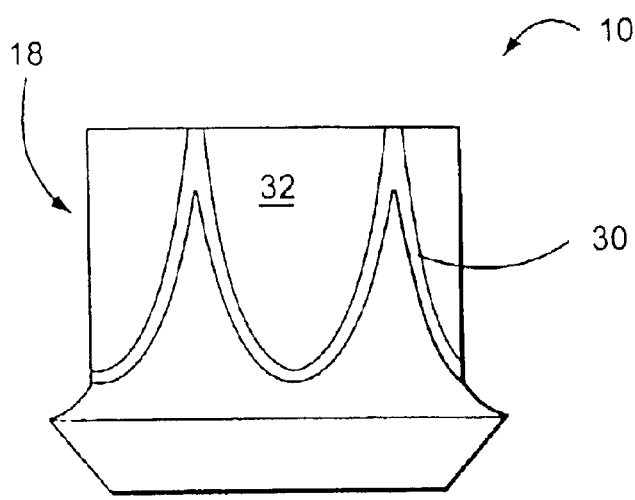
FIG. 3 is a side elevational view of the embodiment of FIG. 1.

Turning now to FIG. 3, tapered projection 18 has a groove 30 formed on exterior surface 32 of tapered projection 18. Groove 30 is preferably inscribed by a computer numerical controlled machine, but alternatively may be formed in any suitable way. Groove 30 is configured to have both a vertical component of an orthogonal system and a horizontal component of the orthogonal system. Alternatively stated, groove 30, taken at most points therealong, will be neither purely vertical nor purely horizontal when abutment 10 is in the orientation shown in FIG. 3. A preferred form of groove 30 is formed by abutting semi-parabolic groove sections wherein the semi-parabola formed by each said groove section opens upwardly. Of course, sections of groove 30 need not define a perfect semi-parabola. Any generally oval or elliptical curve will be suitable.

Figure 4:
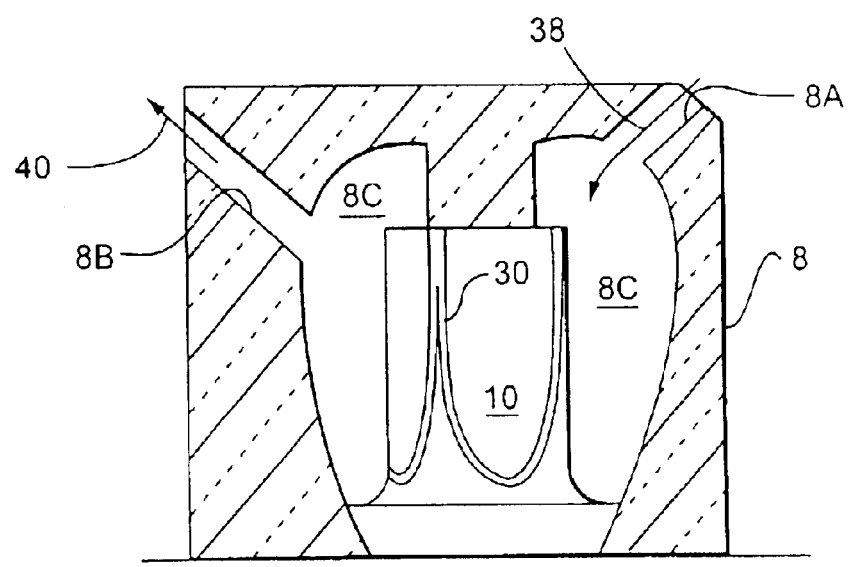
FIG. 4 is an environmental, side cross sectional view of one embodiment of the novel abutment showing casting of a restoration thereon.

FIG. 4 shows evacuation of air as molten metal alloy is being poured into a mold 8 to form restoration 3. Abutment 10 is enclosed within a chamber 8C formed in mold 8. An inflow passage 8A is employed to pour the molten alloy (not shown) into chamber 8C, the direction of flow being indicated by arrow 38. Air being evacuated from chamber 8C is indicated by arrow 40, and flows through an exit passage 8B. Small bubbles (not shown) which could form between projection 18 and restoration 3 are discouraged by improved air flow which occurs as the molten alloy fills chamber 8C, since groove 30 provides a slight additional space for an air flow path.

FIG. 5 illustrates another novel feature of abutment 10. Notably, tapered projection 18 has negative taper such that tapered projection 18 has a relatively small diameter proximate base 16 and a relatively greater diameter away from base 16. The degree of taper is exaggerated for visual clarity in FIG. 5. The preferred degree of taper is less than five degrees, referring to angle 34, and may be as little as one degree. Angle 34 is formed between the vertical axis 36 of stepped bore 12 (see FIG. 1) of abutment 10 and the slope of exterior surface 32 of projection 18, when viewed in side elevation.

It will be noted that wall 7 of restoration 3 (see FIG. 1) is quite thick, even at the bottom. This is a consequence of negative taper of projection 18, and causes the lower end of restoration 3 to have improved strength over conventional restorations (not shown) because of increased wall thickness.

FIGS. 7, 8, and 9 show variations of the grooves which may utilized with the present invention. Looking first at FIG. 7, an abutment 210 has an exaggerated sinusoidal groove 230 formed on its exterior surface 232. In other respects, abutment 210 has characteristics of the abutments of the described embodiments of the invention.

FIG. 8 shows another embodiment of the invention, wherein abutment 310 has one or more discontinuous grooves 330 formed on its exterior surface 332. In other respects, abutment 310 has characteristics of the abutments of the described embodiments of the invention.

FIG. 9 shows still another embodiment of the invention, wherein abutment 410 has a zig-zag groove 430 formed from straight line segments disposed upon its exterior surface 432. In other respects, abutment 410 has characteristics of the abutments of the described embodiments of the invention.

Despite differences in configuration of their respective grooves 230, 330, 430, the embodiments of FIGS. 7, 8, and 9 share the following characteristic among themselves and with all embodiments of the invention. That is, each groove, as it would appear when projected onto a sectional plane of the abutment, extends along its associated abutment in a path which for at least part of the circumference of that abutment is neither purely horizontal nor purely vertical. Alternatively stated, and referring now to FIG. 7, groove 230, when described according to a system of Cartesian coordinates, displays the characteristic that $\Delta x/\Delta y$ is greater than zero and less than infinity for at least part of the circumference of abutment 210. This characteristic prevents rotation of a prosthesis about the abutment, and also prevents the prosthesis from being pulled upwardly, as depicted in FIGS. 3, 7, 8, and 9, out of engagement with its associated abutment.

Figure 6:
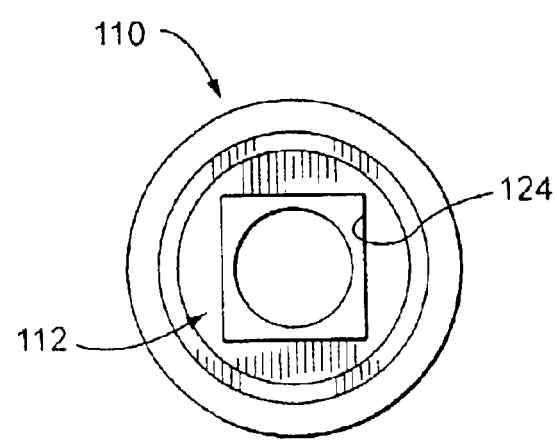
FIG. 6 is a bottom plan view of an alternative view of the invention.

The present invention is susceptible to variations and modifications which may be introduced without departing from the inventive concept. It will be appreciated, for example, that section 24 of stepped bore 12 need not be hexagonal. Rather, section 24 has polygonal configuration opening to the bottom of base 16, for cooperatively receiving a polygonal post of implant 1. It has become frequent practice to employ hexagonal posts (such as element 2 of FIG. 1), although some square posts are offered by the industry. Accordingly, the invention may incorporate a square section 124 of stepped bore 112 into an abutment 110, as shown in FIG. 6. In all other respects, abutment 110 is structurally similar to abutment 10 of FIG. 1. Still other configurations may be employed, so long as interference ensues between the abutment and the implant should a torsional force act on the abutment, such that the configuration prevents the torsional force rotating the abutment relative to the implant.

It is to be understood that the present invention is not limited to the embodiments described above, but encompasses any and all embodiments within the scope of the following claims.

I claim:

1. An abutment for mounting a restoration to a dental implant, comprising:
    a) a base having a relatively great diameter; and
    b) a tapered projection having an exterior surface and a relatively small diameter projecting upwardly and tapering outwardly from said base, wherein said tapered projection and said base have a stepped bore extending axially therethrough, said stepped bore having a relatively large step exposed from said tapered projection and a relatively small step disposed therebelow, wherein said stepped bore has a keyed configuration exposed from below said base, for cooperating with corresponding keyed configuration of the dental implant,
said tapered projection having a substantially semi-parabolic groove formed on said exterior surface thereof, wherein said groove extends along said abutment in a path which for at least part of the circumference of said abutment is neither purely horizontal nor purely vertical.

2. The abutment according to claim 1, wherein said base forms a concave curve where said base joins said tapered projection.

3. The abutment according to claim 1, wherein said groove is formed by abutting semi-parabolic groove sections wherein the semi-parabola formed by each said groove section opens upwardly.

4. The abutment according to claim 1, wherein said tapered projection has negative taper such that said tapered projection has a relatively small diameter proximate said base and a relatively greater diameter away from said base.

5. The abutment according to claim 4, wherein an angle exists between the exterior surface of said tapered projection and the vertical direction, taken when said stepped bore of said abutment is vertically oriented, wherein said angle is less than five degrees.

6. The abutment according to claim 5, wherein said angle is less than two degrees.

7. The abutment according to claim 1, wherein said base has a tapered exterior surface such that said base is relatively wide proximate said tapered projection and is relatively narrow away from said tapered projection.

8. The abutment according to claim 1, wherein said keyed configuration of said stepped bore is polygonal and opens to the bottom of said base, for cooperatively receiving a polygonal post of the dental implant.

9. The abutment according to claim 8, wherein said polygonal configuration of said stepped bore is hexagonal.

10. The abutment according to claim 8, wherein said polygonal configuration of said stepped bore is square.

11. The abutment according to claim 1, wherein said groove is disposed to facilitate removal of fluids by facilitating passage of fluids flowing upwardly along said abutment.

12. The abutment according to claim 1, wherein said stepped bore is configured to enable a screw to fasten said abutment to the implant.

13. An abutment for mounting a restoration to a dental implant, comprising:
    a) a base having a first, relatively great diameter; and
    b) a tapered projection having an exterior surface and a second diameter smaller than said first, relatively great diameter projecting upwardly and outwardly from said base, wherein said tapered projection and said base have a stepped bore extending axially therethrough, said stepped bore having a relatively large step exposed from said tapered projection and a relatively small step disposed therebelow, said stepped bore having a polygonal keyed configuration exposed from below said base, for cooperating with corresponding polygonal keyed configuration of the dental implant, wherein said base forms a concave curve where said base joins said tapered projection, said tapered projection has negative taper such that said tapered projection has a relatively small diameter proximate said base and a relatively greater diameter away from said base, an angle exists between the exterior surface of said tapered projection and the vertical direction, taken when said stepped bore of said abutment is vertically oriented, which angle is less than five degrees, and said base has a tapered exterior surface such that said base is relatively wide proximate said tapered projection and is relatively narrow away from said tapered projection, said tapered projection comprising a groove on an exterior surface thereof and disposed to facilitate removal of fluids.

14. The abutment according to claim 13, wherein said groove extends along said abutment in a path which for at least part of the circumference of said abutment is neither purely horizontal nor purely vertical.

15. The abutment according to claim 13, wherein said stepped bore is configured to enable a screw to fasten said abutment to the implant.

16. An abutment for mounting a restoration to a dental implant, comprising:

a base having a first, relatively great diameter; and a tapered projection having an exterior surface and a second diameter smaller than said first, relatively great diameter, projecting upwardly from said base, wherein said tapered projection and said base have a stepped bore extending axially through both said base and said tapered projection, said stepped bore having a relatively large step exposed from said tapered projection and a relatively small step disposed below said relatively large step, wherein said stepped bore has polygonal keyed configuration exposed from below said base, for cooperating with corresponding polygonal keyed configuration of the dental implant, said tapered projection having a groove formed on said exterior surface thereof and disposed to facilitate removal of fluids, wherein said groove extends along said abutment in a path which for at least part of the circumference of said abutment is neither purely horizontal nor purely vertical, wherein said base forms a concave curve where said base joins said tapered projection, said groove is formed by abutting semi-parabolic groove sections wherein the semi-parabola formed by each said groove section opens upwardly, said tapered projection has negative taper such that said tapered projection has a relatively small diameter proximate said base and a relatively greater diameter away from said base, an angle exists between the exterior surface of said tapered projection and the vertical direction, taken when said stepped bore of said abutment is vertically oriented, wherein said angle is less than five degrees, and said base has a tapered exterior surface such that said base is relatively wide proximate said tapered projection and is relatively narrow away from said tapered projection.

17. The abutment according to claim 16, wherein said stepped bore is configured to enable a screw to fasten said abutment to the implant.

* * * * *